United States Patent [19]

Lindoy et al.

[11] Patent Number: 5,173,210
[45] Date of Patent: Dec. 22, 1992

[54] COMPOSITION AND USE

[75] Inventors: Leonard F. Lindoy, Cranbrook; Darren S. Baldwin, Gulliver, both of Australia; Peter A. Tasker, Oldham, England

[73] Assignee: Imperial Chemical Industries PLC, Millbank, England

[21] Appl. No.: 377,995

[22] Filed: Jul. 11, 1989

[30] Foreign Application Priority Data

Aug. 15, 1988 [GB] United Kingdom ............... 8819375

[51] Int. Cl.$^5$ .............................. C01B 31/16
[52] U.S. Cl. ............................ 252/184; 540/455; 252/180
[58] Field of Search ............... 252/184, 180; 540/455

[56] References Cited

U.S. PATENT DOCUMENTS

| 4,142,020 | 2/1979 | Okamura et al. | 428/403 |
| 4,156,683 | 5/1979 | Lehn | 540/467 |
| 4,917,825 | 4/1990 | McDowell et al. | 252/184 |
| 4,960,882 | 10/1990 | Bradshaw et al. | 540/468 |

FOREIGN PATENT DOCUMENTS 0002970 8/1978 European Pat. Off. .

OTHER PUBLICATIONS

Lindoy "Heavy Metal Chemistry of Mixed Donor Macrocyclic Ligands: Strategies for Obtaining Metal Ion Recognition" Progress in Macrocyclic Chemistry, R. M. Izatt, ed. vol. 3, 99-53-92.
Bartsh et al. "High Lithium Selectivity in Competitive Alkali-Metal Solid Extraction by Lipophyllic Crown Carboxylic Acids" J. A. C. S. 107, 4997-4998 (1985).
Sukhan et al. "Extraction of Copper, Nickel and Cobalt Complexes with Unsaturated Macrocyclic Tetramines and Carboxylic Acids" Ukrainskii Khimicheskii Zhurnal, vol. 49, No. 9, pp. 956-960 (1983).
Morosanova et al. "New Macrocyclic Reagents Containing Nitrogen and Oxygen" Doklady Akademii Nauksssr, Col. 277, No. 5, pp. 1151-1154 Aug. 1984.
Adam et al.; "Ligand Design and Metal-Ion Recognition. Interaction of Nickel(II) with 17- to 19-Membered Macrocycles Containing $O_2N_3$ and $O_3N_2$ Donor Sets and the X-ray Structure of the Parent 17-Membered Macrocyclic Ligand", J.A.C.S., vol. 105, No. 14, (1983) pp. 4645-4651.
Lindoy et al.; "Metal-Ion Recognition. Interaction of $O_2N_2$-Donor Macrocycles with Cobalt (II), Zince (II), and Cadmium (II) and Structure of the Zinc Complex of One Such 15-Membered Macrocycle", Inorg. Chem., vol. 19, No. 11, (1980) pp. 3360-3365.
Adam et al.; "A New Series of Quinquedentate Macrocycles Exhibiting Systematic Donor-Atom Variation: Equilibrium and X-Ray Structural Data for their Interaction with Copper(II)", J. Chem. Soc., Chem. Commun., No. 14, (1987) pp. 1124-1125.
Chem. Abs. vol. 88, No. 13, (1978) pp. 519, 88:89640w.
Izatt et al.; "Effect of Macrocycle Type on the Extraction into Toluene of $Ag^+$, $Pb^{2+}$, and $Cd^{2+}$ Using a Combination of a Macrocycle and Di(2-ethylhexyl)-phosphoric Acid as Extractants", Separation Science and Technology, vol. 21, No. 9, (1986) pp. 865-872.
Adam et al.; "Studies Involving Nitrogen-Oxygen Donor Macrocyclic Ligands. Interaction of Copper(II) with New $O_2N_3$-Donor Macrocycles and the X-Ray Analysis of Aqua(1,12,16-triaza-3,4:9,10-dibenzo-5,-8-dioxacyclo-octadecane)copper(II) Diperchlorate Hydrate", Journal of the Chemical Society, Dalton Transactions Inorganic Chemistry, (1981) pp. 74-79.
Chemical Abstract 104:140952c, "Synthesis and Characterization of Nickel (II) complexes with Potentially Penadentate Macrocyclic Ligands having $N_3O_2$ Donor Sets" Miyokawa et al. Japan 1985.
Chemical Abstract 110:87330u "Metal-Ion Recognition 2, Structural Dislocation Behavior in the Interaction of Zinc (II) and Cadmium (II) with a Series of $O_2N_3$ Donor Macrocycles", Adam et al., Australia, 1988.
Chemical Abstract 109:243130r, "Studies on the New Analytical Methods for Separation and Recovery of Rare Earth Metals (I). Adsorption Characteristics of Uranium (VI) Ion by New Synthetic Resins with Macrocyclic Compounds", Jung et al. Korea, 1988.
Chemical Abstract 99:32140f, "Ligand Design and Metal-Ion Recognition. Interaction of Nickel (II) with 17- to 19-Membered Macrocycles Containing $O_2N_3$ and $O_3N_2$ Donor Sets and the X-ray Structure of the Parent 17-Membered Macrocyclic Ligand" Adam et al. Australia, 1983.

Primary Examiner—Richard D. Lovering
Assistant Examiner—Joseph D. Anthony
Attorney, Agent, or Firm—William E. Dickheiser; Paul L. Sharer

[57] ABSTRACT

A composition comprising a chelating compound which is a macrocyclic compound containing at least two coordinating centers in the ring, at least one of which is a neutral base moiety, and an organic acid containing at least one alkyl or alkenyl group containing 8 or more carbon atoms. The macrocyclic compound contains at least 10 ring atoms and especially at least 12 ring atoms. The neutral base moiety is typically a nitrogen moiety. Preferably there are at least four coordinating centers at least two of which are neutral base moities. The acid can be an alkyl or alkenyl substituted acid for example a long chain carboxylic acid. The composition can be used as an extractant system for the selective extraction of metals from an aqueous phase into an organic phase.

5 Claims, No Drawings

COMPOSITION AND USE

According to the present invention there is provided a composition comprising (a) a chelating compound which is a macrocyclic compound containing at least two coordinating centres in the ring, at least one of which is a neutral base moiety, and (b) an organic acid containing at least one alkyl or alkenyl group containing 8 or more carbon atoms.

The composition is preferably one in which the number of moles of component (b) is at least equal to the number of moles of component (a). Whilst a substantial molar excess of component (b) can be present in the composition, for example a molar ratio of (b) to (a) of 10:1 or more, in general no benefit is gained by the use of such excess quantities of component (b). It is generally preferred that the molar ratio of (b) to (a) does not exceed 5:1 and useful results have been obtained when the molar ratio of (b) to (a) is 2:1 up to 4:1. Conveniently, the number of moles of component (b) should be sufficient to equal the number of neutral base moieties which are present in component (a).

Component (a) of the composition of the present invention is a macrocyclic compound and contains at least 10 ring atoms, and especially at least 12 ring atoms. In general the macrocyclic compound will contain not more than 30 ring atoms. A range of useful macrocyclic compounds contain 14 to 20 ring atoms.

The macrocyclic compound contains at least two coordinating centres in the ring, but it is generally preferred to use a compound having at least four coordinating centres in the ring. Preferred macrocyclic compounds are those which contain at least two neutral base moieties in the ring. The, or each, neutral base moiety is preferably a nitrogen moiety which may be, for example, a tertiary amino (—NR—) or secondary amino grouping (—NH—). The group R in the tertiary amino grouping is a hydrocarbyl group which may optionally be substituted with at least one inert group such as an alkoxy group or halogen atom, which does not adversely affect the coordinating characteristics of the nitrogen moiety. Coordinating centres, which are other than the neutral base moiety, which may be present in the macrocyclic compound include oxygen and sulphur moieties and the like. Particularly preferred macrocyclic compounds which may be used as component (a) of the composition contain two or three nitrogen moieties and two or three further coordinating centres which are oxygen and/or sulphur moieties, for example two oxygen moieties.

The macrocyclic compounds which can be used as component (a) may be represented by the general formula

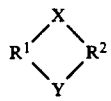

(I)

where

R$^1$ and R$^2$, which may be the same or different, are divalent groups;

X is a neutral base moiety; and

Y is a coordinating centre.

The groups R$^1$ and R$^2$ link X and Y and the linkage may include further coordinating centres. The coordinating centres X and Y, and any further coordinating centres present in R$^1$ and R$^2$, are preferably separated by at least one carbon atom and more generally by two or three carbon atoms. However, the coordinating centres may be separated by more than three carbon atoms, for example by four carbon atoms. In the macrocyclic compounds, the coordinating centres may be separated by the same number of carbon atoms or by different numbers of carbon atoms. Preferably, each of the groups R$^1$ and R$^2$ is, or includes, at least two atoms of an additional cyclic ring such as cyclohexane, cyclohexene, cyclohexadiene or benzene, and most preferably R$^1$ and R$^2$ contain the adjacent ring atoms only of the cyclic ring. The preferred macrocyclic compounds which include at least four coordinating centres may be represented by the general formula

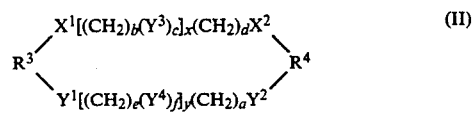

(II)

where

R$^3$ and R$^4$, which may be the same or different, are divalent groups which do not include coordinating centres in the linking atoms, X$^1$ and X$^2$, which may be the same or different, are neutral base moieties Y$^1$, Y$^2$, Y$^3$ and Y$^4$, which may be the same or different, are coordinating centres;

CH$_2$ represents a methylene group;

a is a positive integer;

b is zero or a positive integer;

c is zero or one;

d is a positive integer;

e is zero or a positive integer;

f is zero or one;

x is a positive integer; and y is a positive integer where b and c are both zero or are both positive; and e and f are both zero or are both positive.

The groups X$^1$ and X$^2$ are preferably the same and are —NH— groups or —NR— groups, where R is as hereinbefore defined. The group R can be an alkyl, aryl, alkaryl or aralkyl group or can be an alkaryl or aralkyl group which is further substituted by an aryl or alkyl group respectively. The group R is conveniently a group which contains up to 30 carbon atoms, particularly up to 30 alkyl carbon atoms. The group R may be a benzyl group or an alkyl substituted benzyl group for example 4-alkylbenzyl group such as a 4-t-butylbenzyl group or a 4-dodecylbenzyl group.

Y$^3$ and/or Y$^4$, if present, may be a neutral base moiety and is then preferably the same as X$^1$ and X$^2$. If Y$^3$ and/or Y$^4$, when present, is a coordinating centre other than a neutral base moiety, it is typically oxygen or sulphur and may be the same as, or different from, one or both of the groups Y$^1$ and Y$^2$.

The groups Y$^1$ and Y$^2$ may be neutral base moieties but are preferably either oxygen or sulphur and especially both Y$^1$ and Y$^2$ are oxygen.

The groups R$^3$ and R$^4$ are preferably both the same and are groups —PhCR$^5$R$^6$— where Ph is a 1,2-phenylene group, which may be optionally substituted; and $R^5$ and $R^6$, which may be the same or different, are hydrogen or a hydrocarbyl group, which may be optionally substituted.

The optional substituents in the group Ph are inert groups such as an alkyl group, an alkoxy group or a halogen atom. Any substituent groups in the group Ph are preferably located in the 4-position relative to the group $Y^1$ or $Y^2$. If the substituent is an alkyl group or an alkoxy group, it is conveniently one containing up to 30 carbon atoms, for example up to 24 carbon atoms as in t-butyl, nonyl or dodecyl groups.

The group —$CR^5R^6$— is typically linked to $X^1$ or $X^2$. It is preferred that at least one of the groups $R^5$ or $R^6$ is a hydrogen atom. Compounds in which both of the groups $R^5$ and $R^6$ are hydrogen, that is in which the groups $R^3$ and $R^4$ are —PhCH$_2$—, are generally more readily prepared and hence are generally preferred. If either or both of the groups $R^5$ and $R^6$ are optionally substituted hydrocarbyl groups they may be any of the groups which are disclosed herein as the group R. However it may be preferred that $R^5$ and/or $R^6$ is a lower alkyl group, that is one containing 1 to 4 carbon atoms such as a methyl group.

If the value of both b and c is zero, the group $(CH_2)_b(Y^3)_c$ is absent. However, if both b and c have a positive value, one or more of the groups $(CH_2)_b(Y^3)_c$ is present, depending on the value of x. The value of x is typically one or two and generally is one.

Similarly, if the value of both e and f is zero, the group $(CH_2)_e(Y^4)_f$ is absent. If both e and f are positive, one or more of the groups $(CH_2)_e(Y^4)_f$ is present depending on the value of y. The value of y is typically one or two and generally is one.

The value of a and d, and b and e when these have a positive value, is typically from 1 up to 4 and especially is two or three.

Compounds of formula (II) which can be used as component (a) in the composition of the present invention include, inter alia those set out in Table One hereafter, in all of which $R^3$ and $R^4$ are —PhCH$_2$— (that is $R^5$ and $R^6$ are both hydrogen) where Ph is an unsubstituted 1,2-phenylene group and the CH$_2$ is linked to $X^1$ or $X^2$, e and f are both zero and the value of x is one.

TABLE ONE

| Compound No. | $X^1$ | b | $Y^3$ | c | d | $X^2$ | $Y^2$ | a | $Y^1$ |
|---|---|---|---|---|---|---|---|---|---|
| 1 | NH | zero | — | zero | 3 | NH | O | 2 | O |
| 2 | NH | 2 | NH | 1 | 2 | NH | O | 2 | O |
| 3 | NH | 3 | NH | 1 | 3 | NH | O | 2 | O |
| 4 | NH | 2 | NH | 1 | 2 | NH | O | 1 | O |
| 5 | NH | 2 | S | 1 | 2 | NH | O | 2 | O |
| 6 | NH | 2 | NH | 1 | 2 | NH | O | 4 | O |
| 7 | NH | 2 | NH | 1 | 2 | NH | S | 1 | S |
| 8 | NH | 2 | S | 1 | 2 | NH | S | 1 | S |
| 9 | NH | 2 | NH | 1 | 2 | NH | S | 2 | S |
| 10 | NH | 2 | S | 1 | 2 | NH | S | 2 | S |
| 11 | NH | 2 | NH | 1 | 2 | NH | S | 2 | O |
| 12 | NH | 2 | S | 1 | 2 | NH | S | 2 | O |
| 13 | NH | 2 | O | 1 | 2 | NH | S | 2 | O |
| 14 | NH | 2 | NH | 1 | 2 | NH | O | 3 | O |

Other macrocyclic compounds include derivatives of compounds in Table One, these derivatives being as follows:-

Compound 15 is a modification of compound 1 in which $R^3$ and $R^4$ are —PhCH$_2$— in which Ph is a 1,2-phenylene group having a nonyl group in the 4- position relative to the oxygen atom which is $Y^1$ or $Y^2$.

Compound 16 is a modification of compound 2 in which $R^3$ and $R^4$ are —PhCH$_2$— in which Ph is a 1,2-phenylene group having a t-butyl group in the 4- position relative to the oxygen atom which is $Y^1$ or $Y^2$.

Compound 17 is similar to compound 16 with the exception that the t-butyl group is replaced by a nonyl group.

Compound 18 is a modification of compound 2 in which $X^1$, $Y^3$ and $X^2$ are all the same and are all —NR— groups where R is benzyl (—CH$_2$C$_6$H$_5$).

Compound 19 is similar to compound 18 with the exception $X^1$, $Y^3$ and $X^2$ are all the same and are all —NR— groups where R is 4-t-butylbenzyl (—CH$_2$C$_6$H$_4$ t C$_4$H$_9$).

Compound 20 is similar to compound 18 with the exception $X^1$, $Y^3$ and $X^2$ are all the same and are all —NR— groups where R is 4-dodecylbenzyl (—CH$_2$C$_6$H$_4$C$_{12}$H$_{25}$).

Compound 21 is a modification of compound 2 in which $Y^3$ is a —NR— group where R is 4-dodecylbenzyl.

Compound 22 is a modification of compound 1 in which $R^3$ and $R^4$ are both —Ph CH(CH$_3$)—.

Compound 23 is a modification of compound 2 in which $R^3$ and $R^4$ are both —Ph CH(CH$_3$)—.

A wide range of macrocyclic compounds are known and can be selected to give a desired effect. Compounds of this type are described by Lindoy in "Heavy Metal Chemistry of Mixed Donor Macrocyclic Ligands: Strategies for Obtaining Metal Ion Recognition" in Process in Macrocyclic Chemistry, edited by R. M. Izett and J. J. Christensen, Vol. 3, pages 53 to 92. Compound of this type can be prepared in the manner outlined by Lindoy or in the references noted by Lindoy. Compounds including an alkyl substituted 1,2-phenylene group can be prepared using the corresponding alkyl-substituted hydroxybenzaldehyde. Compounds in which $X^1$, $Y^3$ and $X^2$ are —NR— groups can be obtained by reacting the corresponding macrocyclic compound in which $X^1$, $Y^3$ and $X^2$ are —NH— with the appropriate benzyl halide. The compound in which $Y^3$ is —NR— can be prepared using a triamine containing the group —NR—. The compound in which $R^3$ and $R^4$ are both —Ph CH(CH$_3$)— is prepared using 2-hydroxyacetophenone and an increased reaction time.

The organic acid is conveniently a carboxylic acid since these are generally more readily available. The acid may be a halogen substituted acid such as 2-bromohexadecanoic acid.

The organic acid contains an alkyl or alkenyl group of at least 8 carbon atoms and preferably at least 10 carbon atoms. The alkyl or alkenyl group typically does not contain more than 24 carbon atoms. The alkyl or alkenyl group may be a straight or branched chain group. A mixture of acids can be used having alkyl or alkenyl groups with different numbers of carbon atoms or different isometric alkyl or alkenyl groups, or both. Acids which may be used as component (b) of the composition include nonanoic acid, decanoic acid, dodecanoic acid, tetradecanoic acid, hexadecanoic acid, octadecanoic acid and octadecenoic acid. Acids other than carboxylic acids which may be used include di(2-ethylhexyl) phosphoric acid, dinonylnaphthalene sulphonic acid, dodecylbenzene sulphonic acid and an alkyl sulphonic acid mixture for example a mixture whereof the alkyl groups contain from 13 to 18 carbon atoms with about 95% by weight being alkyl groups containing 14 to 17 carbon atoms.

The compositions of the present invention are soluble in water-immiscible liquid media such as paraffinic hydrocarbons, aromatic hydrocarbons and halohydrocarbons, although the solubility is dependent on the components of the composition and also the nature of the water-immiscible liquid medium. However, the compositions, or the macrocyclic component thereof, are less susceptible to extraction into an aqueous phase than the macrocyclic compound alone under otherwise the same conditions.

The compositions of the present invention are prepared by mixing together the components thereof in the desired proportions. The mixing is conveniently effected in a solvent for the components, particularly a hydrocarbon or halohydrocarbon solvent. The components may be dissolved separately in a solvent and the two solutions then mixed together or one component may be added to a solution of the other component. Mixing may be effected at any suitable temperature and is conveniently effected at ambient temperature although higher temperatures, for example up to 100° C. or more, or lower temperatures, for example 0° C. or lower, may be used if desired or necessary, for example to increase the rate at which a component dissolves.

The macrocyclic component of the composition is preferably one which is capable of forming a complex with a metal and the compositions of the present invention are capable of forming complexes with metals.

Some of the macrocyclic compounds which may be used as a component (a) of the composition of the present invention are believed to be new materials.

Thus, as a further aspect of the present invention there are provided compounds of the general formula II wherein at least one of the groups $R^3$ or $R^4$ is a group —$PhCR^5R^6$ wherein either Ph is a 1,2-phenylene group which is substituted with an alkyl group containing at least 4 carbon atoms; or at least one of the groups $R^5$ and $R^6$ is a phenyl group, a benzyl group or an alkyl group.

Preferred compounds are those in which Ph is a 1,2-phenylene group which is substituted with an alkyl group containing at least six carbon atoms, for example a nonyl or dodecyl group. The substituent group may be a mixture of different groups containing different numbers of carbon atoms or containing mixtures of isomers, for example mixtures of nonyl isomers.

Alternatively, the compound may be one in which one of $R^5$ and $R^6$ is a hydrogen atom and the other is a lower alkyl group, for example, a methyl group.

As a further aspect there are provided compound of the general formula II in which at least one of $X^1$, $Y^3$ and $X^2$ is a group —NR— where R is as defined.

Particular compounds are those in which R is a benzyl group or an alkyl-substituted benzyl group, especially a 4-alkylbenzyl group such as 4-nonylbenzyl or 4-dodecylbenzyl.

A further compound within the present invention is of general formula II in which $R^3$ or $R^4$ is a group —Ph $CR^5R^6$—, where Ph is a 1,2-phenylene group which is substituted with an alkyl group containing at least 4 carbon atoms and at least one of $X^1$, $Y^3$ and $X^2$ is a group —NR— where R is as defined.

Particular compounds of this type are those in which Ph is substituted with a nonyl or dodecyl group and at least one of $X^1$, $Y^3$ and $X^2$ is a group —NR— where R is a benzyl group or a 4-alkylbenzyl group.

The composition of the present invention may be used in systems in which the formation of a metal complex is desirable. Thus, the composition may be used in a solvent extraction process. Alternatively, the composition may be impregnated into a membrane to give a membrane which permits the passage of only certain metal species.

The composition may be used in a solvent extraction process using known solvent extraction procedures.

More specifically, as a further aspect of the present invention there is provided a solvent extraction process for extracting metal values from aqueous solutions of metal salts which comprises the steps of (1) contacting the aqueous solution containing metal salts with a solution of an extractant in a water-immiscible organic solvent, wherein the extractant is a composition comprising components (a) and (b) as hereinbefore described; (2) separating the aqueous solution from the solution of the extractant in the water-immiscible solvent into which metal has been extracted; and (3) contacting the resultant organic phase with an aqueous strip solution whereby the metal transfers into the aqueous strip solution.

The compositions of the present invention form complexes with many metals and the particular metal which can be extracted is dependent on the composition of the aqueous phase, specifically what metals are present, and the particular macrocyclic compound which is present as component (a) of the composition.

Thus, by the determination of metal ion distribution constants in single-metal extraction experiments, and by other procedures, we have found macrocyclic compounds which give compositions which are capable of extracting specific metals from aqueous solution. Thus, when the metal ion is cobalt(II), suitable macrocyclic compounds which can be used as component (a) of the composition include compounds 2, 4, 6, 7 and especially 11, as defined in Table One. When the metal ion is nickel(II), suitable macrocyclic compounds which can be used as component (a) of the composition include compounds 2, 6, 7, 9 and 11, as defined in Table One. When the metal ion is copper(II), suitable macrocyclic compounds include compounds 5, 10, 12, especially 2, 3, 7 and most especially 1, 6, 11 and 14 as defined in Table One, and also compounds 16 and 22 and very preferably compounds 15, 17 and 21 as hereinbefore defined. For both zinc(II) and cadmium(II), suitable macrocyclic compounds which can be used as component (a) of the composition include compounds 2, 3, 4, 7, 9 and 11, as defined in Table One. For silver(I), suitable macrocyclic compounds which can be used as component (a) of the composition include compounds 7 to 13, as defined in Table One and also compounds 18, 19 and 20 as hereinbefore defined. Selective extraction experiments have also been carried out with pairs of metal ions. It has been found that copper(II) is selectively extracted from a mixture of copper(II) and nickel(II) using a composition containing macrocyclic compounds 2, 7, 11 and especially 6, as defined in Table One. It has also been found that cadmium(II) is selectively extracted from a mixture of cadmium(II) and zinc(II) using a composition containing macrocyclic compounds 2 and 11, as defined in Table One. It has also been found that silver is selectively extracted from mixtures of silver and another metal using a composition containing macrocyclic compound 18 as hereinbefore defined and a similar effect may also be obtained using macrocyclic compounds 19 and 20. Using a composition containing macrocyclic compound 17 as hereinbefore defined, copper may be extracted at a lower pH than when using many other macrocyclic compounds and a similar effect may also be obtained using macrocyclic compound 15. It will be appreciated that the foregoing is merely illustrative of macrocyclic compounds which are effective to extract certain metals from an aqueous phase and is not limiting either in respect of the macrocyclic compounds which can be used or the metals which can be extracted. It will also be appreciated that the optimum extraction conditions will depend on the mixture being used, the metals present in the initial aqueous phase and the pH of the extraction stage (step 1) and the pH of the strip stage (step 3).

The solvent extraction process which is a further aspect of the present invention may be incorporated into a wide variety of different methods for the overall recovery of metals from their ores or from other metal-bearing sources. Details of these methods will vary depending on the metal concerned and the nature and composition of the leach solution obtained by leaching the metal from its ore or other source. Whilst the solvent extraction process is not limited to any single overall method for the recovery of metals, it will be appreciated that the solvent extraction process may be only one step in an integrated process for the recovery of the metal from the ore. Such an integrated process may include the following steps:
1. Leaching of the ore with a suitable aqueous solution, and removing any undissolved solids;
2. Contacting the leach solution from step 1, which contains the desired metal in solution, with a solution in a water-immiscible solvent of the composition of components (a) and (b), whereby the metal is transferred into the organic phase;
3. Separating the organic phase containing the extracted metal from the aqueous phase;
4. Contacting the organic phase from step 3 with an aqueous strip solution whereby the metal transfers into the aqueous strip solution;
5. Separating the organic phase containing the stripped extractant from the aqueous strip solution containing a salt of the metal; and
6. Recovering the metal from the strip solution, for example by electrolysing the strip solution from step 5 to recover the metal.

In a fully integrated process of this type it is highly desirable that the solutions be re-circulated between the various stages. Thus aqueous strip solution used in step 4 may be derived from the electrolysis step 6 which is denuded in the metal ion. Similarly the organic phase containing the stripped extractant which is separated in step 5 is preferably re-circulated to the extraction stage 2.

The leaching in stage 1 may be effected using any suitable leaching agent which may be acidic or basic. In stage 2, the composition should be resistant to the species in the leach solution and be capable of extracting the desired metal from the leach solution. This will depend on the choice of both the macrocyclic compound and the organic acid. In stage 4, the aqueous strip solution may be water or an aqueous acid or alkaline solution. The strip solution should be effective to strip the desired metal values from the organic phase without extracting either of components (a) and (b) into the aqueous phase.

With many of the macrocyclic compounds it is convenient to effect extraction and stripping with aqueous solutions having a pH which is in the range from about 1 up to 7, which is not more than, and in general is lower than, the pH of the leach solution.

The composition of the present invention may be used as a solution in many of the water-immiscible organic solvents which have been proposed for use in a solvent extraction process. Such water-immiscible organic solvents include aliphatic, aromatic and alicyclic hydrocarbons and chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point, petroleum fractions (for example kerosene) with varying aromatic content. In general, hydrocarbon solvents having a high aromatic content, for example AROMASOL H which consists essentially of a mixture of trimethylbenzenes and is commercially available from Imperial Chemical Industries PLC (AROMASOL is a registered trade mark), provide a higher solubility for the extractant and the extracted metal whilst kerosene having a relatively low aromatic content, for example ESCAID 100 which is a petroleum distillate comprising 20% aromatics, 56.5% paraffins and 23.4% naphthenes commercially available from ESSO (ESCAID is a registered trade mark) may, in certain cases, improve the hydrometallurgical performance of the extractant.

The concentrations of the macrocyclic compound and the organic acid in the water-immiscible organic solvent may be chosen to suit the particular leach solution to be treated. The concentration of the macrocyclic compound in the organic phase may be up to about 2 Molar, and especially up to 1 Molar in the organic solvent. The concentration of the organic acid is related to the concentration of the macrocyclic compound and typically is such as to provide at least one mole of the organic acid for each mole of the macrocyclic compound.

The extraction stage and the strip stage of the solvent extraction process may conveniently take place at ambient temperature. However it may be possible to improve the net metal transfer from the leach solution to the strip solution if the extraction stage and strip stage are operated at different temperatures, for example if the extraction stage is operated at ambient temperature whilst the strip stage is operated at elevated temperature such as about 50° C.

The invention is illustrated by the following Examples in which all parts and percentages are by weight unless otherwise stated.

Preparation of
6,7,8,9,10,11,17,18-octahydro-5H-dibenzo[e,n]-[1,4]dioxa[8,12]diazacyclopentadecine This is compound 1 as defined in Table One and was prepared by a multistage process of reacting 1,2-dibromoethane with salicylaldehyde; reacting the product with 1,3-diaminopropane and reducing this product with sodium borohydride, using procedures as noted by Lindoy in "Heavy Metal Chemistry of Mixed Donor Macrocyclic Ligands: Strategies for Obtaining Metal Ion Recognition", noted previously herein.

Stage 1: Preparation of
1,4-bis(2-formylphenyl)-1,4-dioxabutane

Salicylaldehyde (97.6 g) was dissolved in 80 cm$^3$ of ethanol. An aqueous solution of sodium hydroxide (32 g) in 1 dm$^3$ of water was added to give a yellow solution. 1,2-dibromoethane (73.6 g) was then added followed by sufficient ethanol to give an homogeneous solution. The mixture was stirred under nitrogen and heated to reflux temperature and maintained at reflux temperature under nitrogen for 44 hours. The mixture was allowed to cool and a solid precipitated. The solid was filtered off and dried. The solid was mixed with hexane at a temperature of about 65° C., sufficient chloroform was added to dissolve the solid and the mixture was allowed to cool and a solid crystallised. The solid had a melting point of 128°-130° C., corresponding closely to the reported melting point of 129° C. for 1,4-bis(2-formylphenyl)-1,4-dioxabutane.

Stage 2: Preparation of 3,4:9,10-dibenzo-1,12-diaza-5,8-dioxacyclopentadecane-1,11-diene A solution of 8.1 g of the product of Stage 1 in methanol (150 cm$^3$) was stirred at ambient temperature and a solution of 1,3-diaminopropane (2.3 g) in methanol (50 cm$^3$) was added dropwise. The solution was stirred, heated to reflux temperature, maintained at reflux temperature for 0.5 hours and distilled water (150 cm$^3$) added. The mixture was cooled to 0°-5° C. for 0.5 hours and a precipitate formed which was filtered off, washed with water and dried at 50° C. A yield of 9 g of 3,4:9,10-dibenzo-1,12-diaza-5,8-dioxacyclopentadecane-1,11-diene was obtained.

Stage 3: Preparation of 6,7,8,9,10,11,17,18-octahydro-5H-dibenzo-[e,n][1,4]dioxa[8,12]diazacyclopentadecine A solution of 2 g of the product of Stage 2 and 0.2 g of disodium tetraborate (borax) in methanol (40 cm$^3$) was stirred and heated to reflux temperature. The mixture was maintained at reflux temperature and 0.6 g of sodium borohydride was added portionwise to the refluxing mixture. After one hour at reflux temperature, the mixture was allowed to cool to ambient temperature, cold water was added and a precipitate which was formed was filtered off.

The solid was recrystallised from a chloroform/hexane mixture as in Stage 1. The solid had a melting point of 144°-146° C., corresponding closely to the reported melting point of 143° C. for 6,7,8,9,10,11,17,18-octahydro-5H-dibenzo[e,n][1,4]dioxa[8,12]diazacyclopentadecine, compound 1 as defined in Table One.

If desired, stages 2 and 3 can be effected without separating a solid product at the end of stage 2. More specifically, after refluxing with the amino compound for an appropriate time, disodium tetraborate is added and then the sodium borohydride is added portionwise to the refluxing mixture. It is generally more convenient to combine stages 2 and 3, particularly if the particularly if the macrocyclic compound is one containing more than 17 atoms in the macrocyclic, that is compounds 3, 6 and 14 in Table One, since with such compounds it has been found that the di-imine product of stage 2 is difficult to isolate as a solid but generally forms an oil.

Compounds 2 to 14 as defined in Table One can be prepared using similar procedures or using procedures described by Lindoy in Progress in Macrocyclic Chemistry, edited by R M Izett and J J Christensen, Vol 3, pages 53 to 92. Compounds 15, 16 and 17 can be prepared in a similar manner by replacing the salicylaldehyde of stage 1 with the corresponding 5-alkyl-2-hydroxybenzaldehyde in an equivalent molar amount.

Compounds 18, 19 and 20 can be prepared from compound 2 by reaction with a benzyl bromide or a 4-alkylbenzylbromide. Exemplary preparations are set out hereafter as Stages 4A and 4B.

Stage 4A: Preparation of 6,9,12-tri(4-t-butylbenzyl)-6,7,8,9,10,11,12,13,19,20-decahydro-5H-dibenzo[e,p,][1,4]dioxa[8,11,14]triazacycloheptadecine 0.68 g of compound 2 (6,7,8,9,10,11,12,13,19,20-decahydro-5H-dibenzo[e,p,][1,4]dioxa[8,11,14]triazacycloheptadecine) were stirred in 10 cm$^3$ of dimethylsulphoxide and 0.5 g of potassium hydroxide were added. 1.4 g of 4-t-butylbenzylbromide were added and the mixture was stirred and heated to reflux temperature and maintained at reflux temperature for two hours.

A white solid precipitated, the mixture was cooled to ambient temperature and the solid was filtered off. The solid was then dissolved in chloroform and the chloroform solution was washed three times with water. The chloroform solution was then dried using anhydrous magnesium sulphate. The chloroform was then evaporated off using a rotary evaporator. 0.8 g of a white solid product was obtained.

Stage 4B: Preparation of 6,9,12-tribenzyl-6,7,8,9,10,11,12,13,19,20-decahydro-5H-dibenzo[e,p][1,4] dioxa[8,11,14]triazacycloheptadecine A solution of 1.41 g of benzyl chloride in 100 cm$^3$ of acetonitrile was added to 2 g of a finely powdered sample of compound 2 and 4.2 g of sodium bicarbonate. The mixture was refluxed overnight. 100 cm$^3$ of dilute hydrochloric acid were added and the aqueous layer was washed twice using 100 cm$^3$ of dichloromethane for each wash. An excess of sodium hydroxide was then added to the aqueous layer to raise the pH to pH 14. The solution was allowed to cool and the reaction products were extracted into dichloromethane which was washed three times with water. The organic phase was then evaporated to dryness. The product obtained was recrystallised from acetonitrile and the crystals obtained were dried over phosphorus pentoxide and then under vacuum (10 mm) overnight.

Compound 21 is prepared using a similar procedure to that described for compound 1 with the exception that the amino compound used in Stage 2 was 4-[4-dodecylbenzyl]diethylenetriamine (the preparation of which is described in Stage 5 hereafter), and Stages 2 and 3 were effected without separating the di-imine product of Stage 2.

Stage 5: Preparation of 4-[4-dodecylbenzyl]diethylenetriamine a) Preparation of di-phthalimido derivative 148.1 g of phthalic anhydride and 51.6 g of diethylene triamine were stirred together in 300 cm$^3$ of xylene and the mixture was stirred and heated to 180° C. The water produced was collected by means of a Dean and Stark leg. After maintaining the mixture at 180° C. for three hours a total of 15 cm$^3$ of water had been collected.

The reaction mixture was allowed to cool, and the solid which precipitated was filtered off. The filtered solid was ground up, washed with xylene and then hexane. The solid was recrystallised from a chloroform/hexane mixture.

b) Preparation of 4-dodecylbenzyl derivative 29.9 g of the phthalimido derivative obtained in (a) were stirred in 500 cm$^3$ of acetonitrile containing 41.4 g of potassium carbonate. 33.9 g of 4-dodecybenzyl bromide were added. The mixture was stirred, heated to reflux temperature, maintained at reflux for 18 hours and then filtered hot.

The filtrate was evaporated using a rotary evaporator and the residue was dissolved in chloroform. The chloroform solution was treated with silica gel, filtered and then evaporated to remove the chloroform leaving a pale yellow oil.

c) Preparation of 4-[4-dodecylbenzyl]diethylenetriamine 52.17 g was the 4-dodecylbenzyl derivative obtained in (b) were dissolved in 500 cm$^3$ of ethanol. Hydrazine hydrate (45 g) was added dropwise.

The mixture was stirred, heated to reflux temperature and maintained under gentle reflux for two hours. The mixture was cooled to ambient temperature and filtered. The filtrate was evaporated using a rotary evaporator. The residue was dissolved in chloroform. The chloroform solution was filtered and washed three times with water using 100 cm$^3$ of water for each wash. The chloroform solution was then dried using anhydrous magnesium sulphate and filtered. The filtrate was evaporated by rotary evaporation to give 32.78 g of a golden yellow oil.

Compound 22 and 23 were prepared using a similar procedure to that described with the exception that salicylaldehyde was replaced by 2-hydroxyacetophenone, in stage 1 reflux temperature was maintained for 48 hours and in stage 2, the reflux temperature was maintained for 48 hours. Stage 3 was effected by adding sodium borohydride to the product mixture from stage 2 (after 48 hours at reflux temperature) without separating product from stage 2. In the preparation of compound 23, diethylenetriamine was used in stage 2.

EXAMPLE 1

Copper(II) acetate (0.04 g) was dissolved in 50 cm$^3$ of distilled water. 0.062 g of compound 1 and 0.08 g of dodecanoic acid were dissolved in 50 cm$^3$ of a mixture of SOLVESSO 150 and n-decanol (containing 10% v/v of n-decanol). The two solutions were stirred vigorously together for two hours and the phases were then allowed to separate and were subjected to analysis for copper.

The following results were obtained:

| | |
|---|---|
| Original copper (II) acetate solution | 250 ppm (w/v) copper |
| Final copper (II) acetate solution | 6 ppm (w/v) copper |
| Organic phase | 235 ppm (w/v) copper. |

For comparison the foregoing procedure was repeated omitting the dodecanoic acid from the organic phase. It was noted that the aqueous phase became more intensely coloured, signifying the formation of a copper complex in the aqueous phase. Dodecanoic acid was then added to the organic phase and the organic phase became coloured whilst the colour was discharged from the aqueous phase.

EXAMPLE 2

A solution of 0.156 g of compound 1 and 1.0 g of dodecanoic acid was formed in 500 cm$^3$ of the SOLVESSO 150/n-decanol mixture. A further solution of 0.1 g of copper(II) acetate was formed in 500 cm$^3$ of distilled water.

50 cm$^3$ of each of the two solutions were stirred together rapidly at ambient temperature for 1.5 hours. Stirring was stopped and the phases were allowed to separate. A blue-green organic phase separated and this was run off. The optical density of the organic solution was measured using a spectrophotometer.

The organic phase was then stirred for one hour at ambient temperature with 50 cm$^3$ of 0.01M aqueous sulphuric acid. When stirring was stopped, a colourless organic phase separated. The organic phase was run off and filtered through Whatman IPS filter paper.

The foregoing procedure was carried out a total of four times, using the same organic phase throughout but using a fresh sample of the aqueous copper(II) acetate solution and of the sulphuric acid for each repeat cycle.

A change of only 1% in the optical density of the organic phase was noted between the first and fourth cycle.

EXAMPLES 3 TO 8

A number of macrocyclic compounds were used in experiments to determine the metal ion distribution of cobalt(II).

In each experiment, 5 cm$^3$ of an aqueous phase and 5 cm$^3$ of an organic phase were shaken together in a sealed, 20 cm$^3$ glass vial using a horizontal shaker operating at 150 oscillations per minute. Shaking was continued for one hour at a controlled temperature of 22°±2° C.

The aqueous phase contained cobalt(II) nitrate at a concentration of $1 \times 10^{-3}$ mol.dm$^3$ in a buffer solution containing $1 \times 10^{-2}$ mol.dm$^{-3}$ of a 2,6-lutedine-3-sulphonic acid/sodium hydroxide mixture. The relative proportions of the components of the buffer mixture were varied depending on the desired pH.

The organic phase was a solution, in chloroform, of $1 \times 10^{-3}$ mol.dm$^{-3}$ of the macrocyclic compound and $4 \times 10^{-3}$ mol.dm$^{-3}$ of hexadecanoic acid.

Control experiments were carried out in the absence of the macrocyclic compound. No detectable extraction was observed in the control experiments.

The metal-ion distribution constants ($D_m$) were calculated by subtracting the amount of metal ion remaining in the aqueous phase at the end of the experiment from that remaining in the aqueous phase of the control experiments. $D_m$ is the ratio of the metal ion concentration in the organic phase at the end of the experiment compared to the sum of the initial metal ion concentration in both phases.

The results obtained are set out in Table Two, in which the compound number corresponds to the compounds as defined in Table One.

TABLE TWO

| | Macrocyclic | $D_m$ | |
|---|---|---|---|
| Example | Compound | pH 4.7 | pH 5.6 |
| 3 | 2 | <0.05 | 0.32 |
| 4 | 3 | <0.05 | 0.16 |
| 5 | 4 | <0.05 | 0.33 |
| 6 | 6 | 0.09 | 0.33 |
| 7 | 7 | <0.05 | 0.29 |
| 8 | 11 | ND | 0.44 |

ND means not determined.

EXAMPLES 9 TO 13

The procedure described for Examples 3 to 8 was repeated with the exceptions that nickel(II) nitrate was used rather than cobalt(II) nitrate, shaking was continued for 40 hours and the pH of the aqueous solution was 4.7.

The results obtained are set out in Table Three.

TABLE THREE

| Example | Macrocyclic Compound | $D_m$ |
| --- | --- | --- |
| 9 | 2 | 0.24 |
| 10 | 6 | 0.39 |
| 11 | 7 | 0.43 |
| 12 | 9 | 0.36 |
| 13 | 11 | 0.41 |

EXAMPLES 14 TO 21

The procedure described for Examples 9 to 13 was repeated with the exceptions that copper(II) nitrate was used rather than nickel(II) nitrate and shaking was continued for one hour.

The results obtained are set out in Table Four.

TABLE FOUR

| Example | Macrocyclic Compound | $D_m$ |
| --- | --- | --- |
| 14 | 2 | 0.57 |
| 15 | 3 | 0.64 |
| 16 | 5 | 0.32 |
| 17 | 6 | 0.87 |
| 18 | 7 | 0.52 |
| 19 | 10 | 0.31 |
| 20 | 11 | 0.90 |
| 21 | 12 | 0.42 |

EXAMPLES 22 TO 27

The procedure described for Examples 3 to 8 was repeated with the exception that zinc(II) nitrate was used rather than cobalt(II) nitrate.

The results obtained are set out in Table Five.

TABLE FIVE

| Example | Macrocyclic Compound | $D_m$ pH 4.7 | $D_m$ pH 5.6 |
| --- | --- | --- | --- |
| 22 | 2 | 0.11 | 0.37 |
| 23 | 3 | 0.13 | 0.42 |
| 24 | 4 | ND | 0.28 |
| 25 | 7 | 0.09 | 0.32 |
| 26 | 9 | ND | 0.34 |
| 27 | 11 | <0.05 | 0.34 |

EXAMPLES 28 TO 33

The procedure described for Examples 3 to 8 was repeated with the exception that cadmium(II) nitrate was used rather than cobalt(II) nitrate.

The results obtained are set out in Table Six.

TABLE SIX

| Example | Macrocyclic Compound | $D_m$ pH 4.7 | $D_m$ pH 5.6 |
| --- | --- | --- | --- |
| 28 | 2 | 0.07 | 0.52 |
| 29 | 3 | <0.05 | 0.32 |
| 30 | 4 | ND | 0.32 |
| 31 | 7 | <0.05 | 0.33 |
| 32 | 9 | ND | 0.56 |
| 33 | 11 | 0.15 | 0.52 |

EXAMPLES 34 TO 40

The procedure described for Examples 3 to 8 was repeated with the exception that silver(I) nitrate was used rather than cobalt(II) nitrate.

The results obtained are set out in Table Seven.

TABLE SEVEN

| Example | Macrocyclic Compound | $D_m$ pH 4.7 | $D_m$ pH 5.6 |
| --- | --- | --- | --- |
| 34 | 7 | 0.56 | 0.87 |
| 35 | 8 | 0.76 | 0.82 |
| 36 | 9 | ND | 0.83 |
| 37 | 10 | ND | 0.92 |
| 38 | 11 | 0.46 | 0.81 |
| 39 | 12 | ND | 0.80 |
| 40 | 13 | ND | 0.84 |

EXAMPLES 41 TO 45

The procedure described for Examples 3 to 8 was repeated with the exception that the aqueous phase contained $0.5 \times 10^{-3}$ mol.dm$^{-3}$ of copper(II) nitrate and $0.5 \times 10^{-3}$ mol.dm$^{-3}$ of nickel(II) nitrate and was buffered to pH 4.7. $D_m$ was determined for each of the metals.

The results obtained are set out in Table Eight.

TABLE EIGHT

| Example | Macrocyclic Compound | $D_m$ Ni (II) | $D_m$ Cu (II) |
| --- | --- | --- | --- |
| 41 | 2 | <0.05 | 0.59 |
| 42 | 5 | <0.05 | 0.20 |
| 43 | 6 | <0.05 | 0.83 |
| 44 | 7 | <0.05 | 0.63 |
| 45 | 11 | <0.05 | 0.65 |

Examples 46 to 48

The procedure described for Examples 41 to 45 was repeated with the exceptions that zinc (II) nitrate and cadmium (II) nitrate were used and the pH was 5.6.

The results obtained are set out in Table Nine.

TABLE NINE

| Example | Macrocyclic Compound | $D_m$ Zn (II) | $D_m$ Cd (II) |
| --- | --- | --- | --- |
| 46 | 2 | 0.07 | 0.55 |
| 47 | 3 | 0.22 | 0.11 |
| 48 | 11 | 0.06 | 0.57 |

It will be noted that the particular metal which is selectively extracted is dependent on the macrocyclic compound.

When the procedure of Examples 46 to 48 was repeated using a pH of 4.7, the value of $D_m$ for both metals was less than 0.1 in all experiments.

Examples 49 to 52

Transport experiments were carried out in a water-jacketed U-tube. In the base of the U-tube was placed 3.6 cm$^3$ of a chloroform solution. In each arm of the tube was located, in contact with the chloroform solution, 3.5 cm$^3$ of an aqueous phase. The chloroform solution was provided with a magnetic stirrer and each aqueous phase was provided with vertically oscillating agitators.

The chloroform phase contained a macrocyclic compound ($1 \times 10^{-3}$ mol.dm$^{-3}$) and hexadecanoic acid ($4 \times 10^{-3}$ mol.dm$^{-3}$).

One aqueous phase contained $5 \times 10^{-2}$ mol.dm$^{-3}$ nickel (II) nitrate and $5 \times 10^{-2}$ mol.dm$^{-3}$ copper (II) nitrate and was buffered to pH 4.7 (as in Examples 3 to 8). The other aqueous phase was buffered to pH 4.7 (as in Examples 3 to 8) and contained 0.1 mol.dm$^{-3}$ of sodium nitrate.

The transfer of the metal ions from one aqueous phase to the other was determined after 100 hours at a temperature of 25°±0.1° C.

The organic/aqueous phase interface was 1.0 cm$^2$. The rate of transfer was determined as mmol.h$^{-1}$ cm$^{3-2}$.

The results obtained are given in Table Ten.

TABLE TEN

| Example | Macrocyclic Compound | Transfer rate | |
|---|---|---|---|
| | | Ni (II) | Cu (II) |
| 49 | 2 | <7 × 10$^{-7}$ | 6.7 × 10$^{-6}$ |
| 50 | 5 | <7 × 10$^{-7}$ | 3.3 × 10$^{-5}$ |
| 51 | 7 | <7 × 10$^{-7}$ | 5.5 × 10$^{-6}$ |
| 52 | 11 | <7 × 10$^{-7}$ | 5.6 × 10$^{-6}$ |

In all cases the rate of transfer of nickel (II) was below the level of detection of the metal.

Examples 53 to 57

The procedure described for Examples 49 to 52 was repeated with the exception that the buffered aqueous solution of sodium nitrate was replaced by a solution containing 0.05 mol.dm$^{-3}$ of ethylenediamine tetraacetic acid which had been adjusted to pH 7.0 by the addition of NaOH.

The results obtained are given in Table Eleven.

TABLE ELEVEN

| Example | Macrocyclic Compound | Transfer rate | |
|---|---|---|---|
| | | Ni (II) | Cu (II) |
| 53 | 2 | <7 × 10$^{-7}$ | 8.9 × 10$^{-5}$ |
| 54 | 5 | <7 × 10$^{-7}$ | 8.8 × 10$^{-5}$ |
| 55 | 6 | <7 × 10$^{-7}$ | 1.5 × 10$^{-4}$ |
| 56 | 7 | <7 × 10$^{-7}$ | 3.8 × 10$^{-5}$ |
| 57 | 11 | <7 × 10$^{-7}$ | 1.6 × 10$^{-4}$ |

EXAMPLES 58 TO 60

The procedure described for Examples 53 to 57 was repeated with the exceptions that the aqueous solution containing nickel(II) and copper(II) was replaced by an aqueous solution containing zinc(II) nitrate and cadmium(II) nitrate and buffered either to pH 4.7 or pH 5.6.

The results obtained are set out in Table Twelve.

TABLE TWELVE

| Ex | Macrocyclic Compound | Transfer rate | | | |
|---|---|---|---|---|---|
| | | pH 4.7 | | pH 5.6 | |
| | | Zn (II) | Cd (II) | Zn (II) | Cd (II) |
| 58 | 2 | 6.9 × 10$^{-7}$ | 2.6 × 10$^{-5}$ | 2.1 × 10$^{-6}$ | 6.6 × 10$^{-5}$ |
| 59 | 3 | 5.8 × 10$^{-6}$ | 4.3 × 10$^{-7}$ | 3.4 × 10$^{-5}$ | 4.0 × 10$^{-6}$ |
| 60 | 11 | 7.9 × 10$^{-7}$ | 5.7 × 10$^{-5}$ | 1.3 × 10$^{-6}$ | 7.9 × 10$^{-5}$ |

EXAMPLE 61

Copper(II) nitrate (0.12 g) was dissolved in 50 cm$^3$ of distilled water. 0.169 g of compound 2 and 0.256 g of hexadecanoic acid were dissolved in 50 cm$^3$ of a mixture of SOLVESSO 150 and n-decanol (containing 10% v/v of n-decanol). The two solutions were stirred vigorously together for two hours and the phases were then allowed to separate. The aqueous phase was deep blue and the organic phase was essentially colourless.

The procedure was repeated except that compound 2 and the hexadecanoic acid were dissolved in Escaid 100. A similar result was obtained.

The procedure was repeated except that compound 2 and the hexadecanoic acid were dissolved in chloroform. The aqueous phase was pale blue and the organic phase was deep blue.

EXAMPLE 62

The various experiments described in Example 61 were repeated using an equivalent molecular proportion of compound 14 as the macrocyclic compound. The results obtained were similar to those obtained in Example 61.

EXAMPLE 63

The first experiment of Example 61 was repeated using an equivalent molecular proportion of compound 15 as the macrocyclic compound. The aqueous phase was essentially colourless and the organic phase was pale green.

Using chloroform as the organic solvent, a similar result was obtained.

EXAMPLE 64

The experiments described in Example 61 were repeated using an equivalent molecular proportion of compound 16 as the macrocyclic compound. In all cases the organic phase was a deep red-blue in colour and the aqueous phase was essentially colourless.

EXAMPLE 65

The experiments described in Example 61 were repeated using an equivalent molecular proportion of compound 17 as the macrocyclic compound. The results obtained were similar to those obtained in Example 64.

EXAMPLE 66

The first experiment of Example 61 was repeated using an equivalent molecular proportion of compound 21 as the macrocyclic compound. The organic phase was a deep blue in colour and the aqueous phase was essentially colourless.

EXAMPLES 67 to 73

The procedure of Examples 3 to 8 was repeated using an equivalent molecular proportion of compound 18 as the macrocylic compound. The aqueous phase contained 1×10$^{-3}$ mol dm$^{-3}$ of a different metal nitrate in each experiment. The pH of the aqueous solution in all experiments was buffered to a pH of 5 using a mixture of 2 molar acetic acid and 2 molar sodium acetate as the buffer. The transfer time was 24 hours.

The metal ion distribution constants were determined for each metal and the results are set out in Table Thirteen.

TABLE THIRTEEN

| Example | Metal | $D_m$ |
|---|---|---|
| 67 | Ag$^+$ | 0.130 |
| 68 | Pb$^{2+}$ | 0.024 |
| 69 | Zn$^{2+}$ | 0.007 |
| 70 | Cd$^{2+}$ | 0.035 |
| 71 | Ni$^{2+}$ | 0.000 |
| 72 | Co$^{2+}$ | 0.028 |
| 73 | Cu$^{2+}$ | 0.023 |

The amount of nickel ion extracted was below the limit of detection and hence is reported as giving no extraction.

EXAMPLES 74 to 81

Transport experiments were carried out in a manner similar to that described for Examples 49 to 52.

The experiments were carried out in a beaker of diameter 5.7 cm having an open tube of internal diameter 2.5 cm located vertically within the beaker. 50 cm$^3$ of a chloroform solution containing macrocyclic compound 18 ($1 \times 10^{-3}$ mol.dm$^{-3}$) and hexadecanoic acid ($4 \times 10^{-3}$ mol.dm$^{-3}$) were placed in the beaker, the lower end of the open tube being immersed in the chloroform solution with clearance between the lower end of the tube and the base of the beaker. Within the tube were placed 10 cm$^3$ of an aqueous source phase which contained $5 \times 10^{-3}$ mol.dm$^{-3}$ of a metal salt and which was buffered to pH 5 using an acetic acid/sodium acetate mixture as in Examples 67 to 73. Around the outside of the tube were placed 30 cm$^3$ of an aqueous receiving phase which was buffered to pH3 using a mixture of formic acid and sodium hydroxide. The chloroform solution was in contact with both of the aqueous phases but the only contact between the aqueous phases was through the chloroform solution.

The chloroform solution was stirred by means of a magnetic stirring bar rotating at 120 r.p.m. The aqueous phases were not stirred.

The concentration of the metal in the receiving aqueous phase was determined after 24 hours at 25° C. The results are set out in Table Fourteen.

TABLE FOURTEEN

| Example | Metal | Concentration in Receiving phase (mol · dm$^{-3}$) |
|---|---|---|
| 74 | Ag$^+$ | 5.91 × 10$^{-4}$ |
| 75 | Pb$^{2+}$ | 4.15 × 10$^{-6}$ |
| 76 | Cu$^{2+}$ | 3.16 × 10$^{-5}$ |
| 77 | Ni$^{2+}$ | 0.00 |
| 78 | Co$^{2+}$ | 1.60 × 10$^{-6}$ |
| 79 | Zn$^{2+}$ | 3.06 × 10$^{-7}$ |
| 80 | Cd$^{2+}$ | 1.78 × 10$^{-7}$ |
| 81 | Hg$^{2+}$ | 1.99 × 10$^{-5}$ |

The amount of nickel ion in the receiving phase was below the limit of detection and hence is reported as giving no extraction.

EXAMPLE 82 to 91

The transport experiments of Examples 74 to 81 were repeated with the exception that in all cases the aqueous source phase contained two metals, one of which was silver. Each of the metals was present in the source phase at a concentration of 10$^{-2}$ mol.dm$^{-3}$. The competitive transport rate was determined by determination of the concentration of each metal in the aqueous receiving phase at the end of each experiment. The results are set out in Table Fifteen.

TABLE FIFTEEN

| Example | Second Metal | Relative Concentration |
|---|---|---|
| 82 | Mn | 2369 |
| 83 | Mg | 1930 |
| 84 | Hg | 0.717 |
| 85 | Ca | 505 |
| 86 | Cu | 72 |
| 87 | Pb | 468 |
| 88 | Ni | 927 |

TABLE FIFTEEN-continued

| Example | Second Metal | Relative Concentration |
|---|---|---|
| 89 | Cd | 15760 |
| 90 | Zn | 1576 |
| 91 | Co | 3864 |

Relative concentration is the concentration of silver in the aqueous receiving phase divided by the concentration of the second metal in the aqueous receiving phase.

EXAMPLES 92 to 119

A series of experiments was carried out using either compound 2, compound 16 or compound 17 as the macrocyclic compound. The procedure used was as described for Example 1 with the exception that an equivalent molecular proportion of copper(II) nitrate was used and an equivalent molecular proportion of the appropriate macrocyclic compound was used.

The organic solution and the aqueous solution were stirred together to form an emulsion and stirring was continued for a sufficient time to allow the pH of the emulsion to stabilise. The pH of the emulsion was measured using a pH meter, stirring was stopped and the two phases were allowed to separate. A sample of the organic phase was removed by pipette and filtered through Whatman 1PS phase separation paper to remove any entrained aqueous phase. The organic solution was transferred to a 10 mm quartz cell. The absorbance of the solution was measured using a Perkin-Elmer Lambda 15 u.v./visible spectophotometer and the absorption peak height was recorded.

The organic solution was returned to the vessel containing the organic and aqueous phases. The contents of the vessel were stirred and the pH pf the emulsion was adjusted by the addition of dilute nitric acid or dilute aqueous sodium hydroxide solution as required.

The procedure was repeated several times to determine the variation of the optical density (absorbance) of the organic phase with variation of pH of the emulsion.

The variation of optical density of the organic phase with the pH of the emulsion is set out in Table Sixteen.

TABLE SIXTEEN

| Macrocycle 2 | | Macrocycle 16 | | Macrocycle 17 | | | | |
|---|---|---|---|---|---|---|---|---|
| Ex | pH | OD | Ex | pH | OD | Ex | pH | OD |
| 92 | 11.0 | 1.44 | 101 | 5.7 | 1.58 | 111 | 4.8 | 1.70 |
| 93 | 8.8 | 1.44 | 102 | 5.3 | 1.59 | 112 | 4.4 | 1.63 |
| 94 | 8.0 | 1.40 | 103 | 4.7 | 1.6 | 113 | 3.5 | 1.56 |
| 95 | 6.6 | 1.25 | 104 | 3.9 | 1.48 | 114 | 3.2 | 1.46 |
| 96 | 6.2 | 1.06 | 105 | 3.7 | 1.34 | 115 | 3.0 | 1.12 |
| 97 | 5.7 | 0.74 | 106 | 3.4 | 0.84 | 116 | 2.7 | 0.60 |
| 98 | 4.4 | 0.11 | 107 | 3.2 | 0.47 | 117 | 2.5 | 0.30 |
| 99 | 4.0 | 0.06 | 108 | 2.9 | 0.17 | 118 | 2.2 | 0.11 |
| 100 | 3.6 | 0.0 | 109 | 2.7 | 0.10 | 119 | 2.0 | 0.0 |
| | | | 110 | 1.8 | 0.0 | | | | pH is the pH of the emulsion before the organic phase is separated. OD is the optical density (absorbance) of the organic phase, determined as described.

EXAMPLE 120

The procedure of Examples 92 to 119 was repeated using compound 16 as the macrocyclic compound. The optical density of the organic phase was determined and samples of the organic phase were analysed for copper content. Two curves were drawn, one of optical density of the organic phase against pH of the aqueous solution and the other of copper content of the organic phase against pH of the aqueous solution. A very close correlation between the two curves was noted.

EXAMPLES 121 to 125

The procedure of Examples 111 to 119 was repeated using 0.296 g of macrocyclic compound 17 and 0.335 g of 2-bromohexadecanoic acid in 50 cm³ of a mixture of SOLVESSO 150 and n-decanol (containing 10% v/v of n-decanol).

The variation of optical density of the organic phase with the pH of the emulsion is set out in Table Seventeen.

TABLE SEVENTEEN

| Example | pH | OD |
|---|---|---|
| 121 | 3.39 | 1.36 |
| 122 | 2.82 | 0.99 |
| 123 | 2.44 | 0.39 |
| 124 | 2.27 | 0.15 |
| 125 | 2.04 | 0.0 |

EXAMPLE 126

A solution of 2.96 g of compound 17 and 2.56 g of hexadecanoic acid was formed in 500 cm³ of the SOLVESSO 150/n-decanol mixture. A further solution of 1.205 g of copper(II) nitrate was formed in 500 cm³ of distilled water.

50 cm³ of each of the two solutions were stirred together rapidly at ambient temperature for 1.5 hours. Stirring was stopped and the phases were allowed to separate. A blue-green organic phase separated and this was run off. The optical density of the organic solution was measured using a spectrophotometer.

The organic phase was then stirred for one hour at ambient temperature with 50 cm³ of 0.01M aqueous sulphuric acid. When stirring was stopped, a colourless organic phase separated. The organic phase was run off and filtered through Whatman IPS filter paper.

The foregoing procedure was carried out a total of three times, using the same organic phase throughout but using a fresh sample of the aqueous copper(II) nitrate solution and of the sulphuric acid for each repeat cycle.

A change of only 1% in the optical density of the organic phase was noted between the first and third cycle.

We claim:

1. A composition which comprises:
   (a) a chelating compound which is a macrocyclic compound having at least 12 and not more than 30 ring atoms and containing two or three nitrogen moieties and two or three further coordinating centers which are oxygen and/or sulphur moieties: and
   (b) a carboxylic acid which contains at least one alkyl or alkenyl group having 8 or more carbon atom wherein said composition contains at least one mole of component (b) for each mole of component (a).

2. The composition of claim 1 wherein component (a) has the general formula

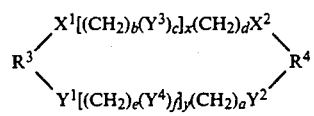

where
$R^3$ and $R^4$, which may be the same or different, are divalent groups which do not include coordinating centres in the linking atoms;
$X^1$ and $X^2$, which may be the same or different, are neutral base moieties;
$Y^1$, $Y^2$, $Y^3$ and $Y^4$, which may be the same or different, are coordinating centres;
$CH_2$ represents a methylene group;
a is a positive integer;
b is zero or a positive integer;
c is zero or one;
d is a positive integer;
e is zero or a positive integer;
f is zero or one;
x is a positive integer; and
y is a positive integer
where
b and c are both zero or are both positive; and
e and f are both zero or are both positive.

3. The composition of claim 2 wherein, in component (a), $X^1$ and $X^2$ are both —NH— groups or are both —NR— groups,
where
R is a hydrocarbyl group which is optionally substituted with at least one alkoxy group or halogen atom.

4. The composition of claim 2 wherein, in component (a), each of the groups $R^3$ and $R^4$ is a group —PhCR$^5$R$^6$— where Ph is a 1,2-phenylene group which may be substituted with an alkyl group, an alkoxy group or a halogen atom; and $R^5$ and $R^6$, which may be the same or different, are hydrogen or a hydrocarbyl group which may be substituted with at least one alkoxy group or halogen atom.

5. The composition of claim 2 wherein component (a) is a macrocyclic component selected from the group consisting of compound 1 to 23 wherein all of said compounds, e and f are both zero; and x is 1; and wherein, in compounds 1-14, $R^3$ and $R^4$ are —PhCH$_2$— wherein Ph is an unsubstituted 1,2-phenylene group and the CH$_2$ is linked to $X^1$ or $X^2$; and wherein $X^1$, b $Y^3$, c, d, $X^2$, $Y^2$, a and $Y^1$ are as follows:

| Compound No. | $X^1$ | b | $Y^3$ | c | d | $X^2$ | $Y^2$ | a | $Y^1$ |
|---|---|---|---|---|---|---|---|---|---|
| 1 | NH | zero | — | zero | 3 | NH | O | 2 | O |
| 2 | NH | 2 | NH | 1 | 2 | NH | O | 2 | O |
| 3 | NH | 3 | NH | 1 | 3 | NH | O | 2 | O |
| 4 | NH | 2 | NH | 1 | 2 | NH | O | 1 | O |
| 5 | NH | 2 | S | 1 | 2 | NH | O | 2 | O |
| 6 | NH | 2 | NH | 1 | 2 | NH | O | 4 | O |
| 7 | NH | 2 | NH | 1 | 2 | NH | S | 1 | S |
| 8 | NH | 2 | S | 1 | 2 | NH | S | 1 | S |
| 9 | NH | 2 | NH | 1 | 2 | NH | S | 2 | S |
| 10 | NH | 2 | S | 1 | 2 | NH | S | 2 | S |
| 11 | NH | 2 | NH | 1 | 2 | NH | S | 2 | O |
| 12 | NH | 2 | S | 1 | 2 | NH | S | 2 | O |
| 13 | NH | 2 | O | 1 | 2 | NH | S | 2 | O |
| 14 | NH | 2 | NH | 1 | 2 | NH | O | 3 | O | and wherein

Compound 15 is a modification of compound 1 in which $R^3$ and $R^4$ are —$PhCH_2$— in which Ph is a 1,2-phenylene group having a nonyl group in the 4-position relative to the oxygen atom which is $Y^1$ or $Y^2$;

Compound 16 is a modification of compound 2 in which $R^3$ and $R^4$ are —$PhCH_2$— in which Ph is a 1,2-phenylene group having a t-butyl group in the 4-position relative to the oxygen atom which is $Y^1$ or $Y^2$;

Compound 17 is similar to compound 16 with the exception that the t-butyl group is replaced by a nonyl group;

Compound 18 is a modification of compound 2 in which $X^1$, $Y^3$ and $X^2$ are all the same and are all —NR— groups where R is benzyl (—$CH_2C_6H_5$);

Compound 19 is similar to compound 18 with the exception $X^1$, $Y^3$ and $X^2$ are all the same and are all —NR— groups where R is 4-t-butylbenzyl (—$CH_2C_6H_4$ t $C_4H_9$);

Compound 20 is similar to compound 18 with the exception $X^1$, $Y^3$ and $X^2$ are all the same and are all —NR— groups where R is 4-dodecylbenzyl (—$CH_2C_6H_4C_{12}H_{25}$);

Compound 21 is a modification of compound 2 in which $Y^3$ is a —NR— group where R is 4-dodecylbenzyl;

Compound 22 is a modification of compound 1 in which $R^3$ and $R^4$ are both —Ph $CH(CH_3)$—; and Compound 23 is a modification of compound 2 in which $R^3$ and $R^4$ are both —Ph $CH(CH_3)$—.

* * * * *